United States Patent
Kawabata et al.

(10) Patent No.: US 10,024,801 B2
(45) Date of Patent: Jul. 17, 2018

(54) ANALYSIS SYSTEM FOR ONLINE-TRANSFERRED ANALYSIS SAMPLE

(71) Applicant: IAS Inc., Tokyo (JP)

(72) Inventors: Katsuhiko Kawabata, Tokyo (JP); Tatsuya Ichinose, Tokyo (JP); Mitsumasa Ikeuchi, Tokyo (JP)

(73) Assignee: IAS Inc., Tokyo (JP)

( * ) Notice: Subject to any disclaimer, the term of this patent is extended or adjusted under 35 U.S.C. 154(b) by 0 days.

(21) Appl. No.: 15/540,320

(22) PCT Filed: Aug. 16, 2016

(86) PCT No.: PCT/JP2016/073880
§ 371 (c)(1),
(2) Date: Jun. 28, 2017

(87) PCT Pub. No.: WO2017/033796
PCT Pub. Date: Mar. 2, 2017

(65) Prior Publication Data
US 2018/0024068 A1    Jan. 25, 2018

(30) Foreign Application Priority Data
Aug. 21, 2015   (JP) ................... 2015-163751

(51) Int. Cl.
*G01N 21/73*   (2006.01)
*H01J 49/10*   (2006.01)
(Continued)

(52) U.S. Cl.
CPC ............. *G01N 21/68* (2013.01); *G01N 21/73* (2013.01); *G01N 21/85* (2013.01); *G01N 27/62* (2013.01);
(Continued)

(58) Field of Classification Search
CPC ........ G01N 21/73; G01N 21/39; G01N 21/66; G01N 21/714; G01N 2030/202;
(Continued)

(56) References Cited

U.S. PATENT DOCUMENTS 4,804,519 A * 2/1989 Sainz ..................... G01N 1/38
356/316
6,126,086 A * 10/2000 Browner ................. B05B 7/066
239/102.1
(Continued)

FOREIGN PATENT DOCUMENTS

JP   S62-298749 A   12/1987
JP   5-296933 A     11/1993
(Continued)

OTHER PUBLICATIONS

European Search Report for EP16839143.
International Search Report for PCT/2016/073880.

*Primary Examiner* — David A Vanore
(74) *Attorney, Agent, or Firm* — Roberts & Roberts, LLP

(57) ABSTRACT

The present invention relates to an analysis system capable of online transferring an analysis sample and promptly acquiring an analysis result. The analysis system capable of analyzing the analysis samples supplied from at least two sites, with one analysis apparatus, and requiring no cleaning process for a nebulizer and a spray chamber, is provided. The present invention relates to analysis system including at least two sample individually transferring units. Each sample transferring path of the sample individually transferring units is coupled to a plasma torch of a common analysis unit including the one analysis apparatus with inductively-coupled plasma or microwave plasma. Each sample transferring path has a main flow path, a makeup gas supply path, and a drain flow path. The plasma torch has a sample introducing pipe that introduces the atomized analy- (Continued)

sis sample, provided at a substantially center. The inner diameter of the drain flow path is equivalent to or larger than the inner diameter of an inlet portion of the sample introducing pipe of the plasma torch.

10 Claims, 2 Drawing Sheets

(51) Int. Cl.
*G01N 21/68* (2006.01)
*G01N 21/85* (2006.01)
*G01N 27/62* (2006.01)
*G01N 21/84* (2006.01)
*G01N 1/00* (2006.01)
*G01N 1/10* (2006.01)

(52) U.S. Cl.
CPC ...... *H01J 49/105* (2013.01); *G01N 2001/002* (2013.01); *G01N 2001/1006* (2013.01); *G01N 2021/8411* (2013.01)

(58) Field of Classification Search
CPC ....... G01N 2030/201; G01N 2030/207; G01N 15/1031; G01N 15/1459; G01N 35/08; G01N 35/085; G01N 35/1095; G01N 2015/1006; G01N 2015/1043; G01N 2015/1062; G01N 2015/1486; H01J 49/105; H01J 49/0431; H01J 49/0495; H01J 49/067; H01J 49/10; H01J 49/165; H01J 49/168; H01J 49/26

USPC .............. 356/316, 319, 437; 250/336.1, 395, 250/423 R, 424, 428; 422/54, 81, 82.09

See application file for complete search history.

(56) References Cited

U.S. PATENT DOCUMENTS

| | | | |
|---|---|---|---|
| 9,146,182 B1* | 9/2015 | Wiederin | G01N 30/20 |
| 9,541,207 B1* | 1/2017 | Saetveit | F16K 11/0743 |
| 2004/0160605 A1* | 8/2004 | Wang | G01J 3/42 |
| | | | 356/437 |
| 2014/0331861 A1* | 11/2014 | Makarov | H01J 49/067 |
| | | | 95/90 |
| 2016/0172178 A1* | 6/2016 | Apffel | G01N 35/08 |
| | | | 250/395 |
| 2017/0162373 A1* | 6/2017 | Field | G01N 1/38 |

FOREIGN PATENT DOCUMENTS

| | | |
|---|---|---|
| JP | H05-296933 A | 11/1993 |
| JP | 6-109638 A | 4/1994 |
| JP | H06-109638 A | 4/1994 |
| JP | 10-106483 A | 4/1998 |
| JP | 2000-100374 A | 4/2000 |
| JP | 2004-286604 A | 10/2004 |
| JP | 3815322 B2 | 8/2006 |
| WO | 98/29896 A | 7/1998 |

* cited by examiner (a)

(b)

ANALYSIS SYSTEM FOR ONLINE-TRANSFERRED ANALYSIS SAMPLE

TECHNICAL FIELD

The present invention relates to a system that online transfers at least two analysis samples and performs analysis with one analysis apparatus. Particularly, the present invention relates to a system suitable to analysis with inductively-coupled plasma or microwave plasma.

BACKGROUND ART

There is a need to analyze the concentration of a trace metal in a solution for quality control and drainage management in a factory for various treatment liquids or chemicals during a semiconductor manufacturing process. Additionally, the analysis of a trace element is required for environmental analysis of water quality control of a river or soil contamination. An analysis apparatus with inductively-coupled plasma (ICP) (hereinafter, referred to as an ICP analysis apparatus, in some cases), such as an inductively-coupled plasma mass spectrometry apparatus, or an analysis apparatus with microwave plasma (MP) (hereinafter, referred to as an MP analysis apparatus), such as an inductively-coupled plasma optical emission spectrometry apparatus, is used for the analysis of the trace element. The ICP analysis apparatus or the MP analysis apparatus is often installed in analysis facilities, such as a research institute or a laboratory. Typically, an analysis sample collected at a site, such as a factory, is delivered to the laboratory, and a trace element is analyzed.

In this manner, the element analysis with, for example, the ICP analysis apparatus, is not directly performed in the field generally, and the analysis sample is delivered through human hands causing a time lag occurs until an analysis result is acquired. Accordingly, even when abnormality is detected from the analysis result, feedback to the site, such as a production line, is delayed and defective products are manufactured during the delay, thereby raising a problem that a trouble cannot be completely prevented from occurring. Further, the analysis sample is collected through human hands, thereby limiting the frequency with which the analysis can be made and additionally may cause a problem in safety of an operator in some types of acid, alkali, or organic solvent used in the production line.

In consideration of the background, an analysis system capable of online transferring the analysis sample from the site to the ICP analysis apparatus or the MP analysis apparatus, is desired. Regarding this point, an online transferring unit that periodically or continuously samples a sample solution during a manufacturing process, is proposed for a liquid chromatograph spectrometry apparatus that is different from the ICP analysis apparatus in terms of device type, in Patent Document 1. The system is capable of omitting a large-scale driving mechanism due to installation of a flow path switching valve.

As described above, one analysis apparatus is ideally installed in each site in which an analysis sample is sampled, in a system that online transfers the analysis sample. However, the number of the ICP analysis apparatuses or MP analysis apparatuses that can be installed in one facility is limited, and introducing the analysis apparatus in a quantity equivalent to the number of sampling sites is difficult. This is because the ICP analysis apparatus is relatively a large precision equipment, an installing space or an air-conditioning environment is limited, a place in which the analysis apparatus can be installed is restrictive, and additionally an apparatus cost is expensive. In consideration of the above circumstances, an analysis system including the ICP analysis apparatus or the MP analysis apparatus preferably has a configuration in which one or a small number of the ICP analysis apparatuses can analyze analysis samples sampled from a plurality of sites.

Here, as illustrated in FIG. 1, an analysis system with, for example, the ICP analysis apparatus, typically atomizes a sample solution S in a liquid state with a nebulizer N, traps fog having a large particle diameter in a spray chamber C, introduces only an analysis sample having a small particle diameter in a fog state (an average particle diameter of approximately 5 μm) to a plasma torch P, and then provides the analysis sample for mass analysis or spectroscopic analysis. When the analysis system analyzes different samples collected at a plurality of sites, it can be thought that a sample solution to be supplied to the nebulizer is appropriately replaced with another (e.g., a supply tube is changed with another) as a simplest way. However, in this case, sufficiently cleaning the inside of each of the nebulizer and the spray chamber is necessary before one sample solution that has been analyzed is replaced with another sample solution. When the different analysis samples mix inside, for example, the spray chamber, an accurate analysis result is not acquired. When the samples are different from each other in liquidity, a deposit easily occurs (e.g., salt deposits when an acid solution and an alkali solution mix).

With respect to the cleaning for the inside of the spray chamber, Patent Document 2 discloses an analysis system including an introducing portion for a sample solution and an introducing portion for a cleaning liquid, coupled to one spray chamber. The system includes the two liquid introducing portions provided so that time necessary for cleaning the inside of the spray chamber can be reduced in analyzing at least two types of analysis samples.

RELATED ART DOCUMENT

Patent Documents

Patent Document 1: JP 3815322 B2
Patent Document 2: JP 2004-286604 A

SUMMARY OF THE INVENTION

Problems to be Solved by the Invention

In the conventional art, a hexagonal valve is applied to the system in Patent Document 1 and a peristaltic pump is applied to the system in Patent Document 2. In this manner, a conventional system includes a "pump" or a "valve" for making a switch of a plurality of flow paths or introducing a sample smoothly, in a supply path of the analysis sample. However, there is a problem that the pump and the valve have a dead volume portion in which the analysis sample is easily retained. In a case where a plurality of analysis samples are analyzed, when an analysis sample remains inside the dead volume, a previously-measured analysis sample will mix in trace quantities with another subsequently-measured analysis sample, thereby interfering in a detection value and an analysis result is susceptible to error. This type of phenomenon is referred to as a "memory effect". When the ICP analysis apparatus or the MP analysis apparatus analyzes a trace sample at the ppt level, mixing of the trace sample easily and considerably influences a measurement result so that the memory effect is specifically severe. When a sample having a low concentration is analyzed after a sample having a high concentration (a high matrix) is measured, an error easily occurs in a measurement result in a case where the memory effect occurs. Note that, the memory effect may occur in a configuration including various components having a dead volume portion, provided in the flow path of the analysis samples, other than the pump and the valve.

The system in Patent Document 1 online transfers the analysis sample in a "liquid state" so that there is a risk that the analysis sample comes in contact with a laying pipe during transfer and sample loss or contamination occurs. Specifically, metal in a solution having a high dissociation constant, barely varies in an ionic state and an element adsorbs to small cavities on an inner wall of the laying pipe for the transfer so that the sample loss occurs. Particularly, when the analysis sample is an alkali solution, the adsorption of the metal element easily occurs. When the laying pipe for the analysis sample is made of resin, a fine particle in the analysis sample (an object to be measured) is taken in small cavities on a surface of the laying pipe so that the loss may occur. Furthermore, in contrast to the above, an unintended metal element or organic component resulting from a constituent material of the laying pipe or extraneous matter of the inner wall of the laying pipe, mixes with the analysis sample, from the inner wall of the laying pipe in contact so that the contamination may occur.

Here, when a small number of analysis apparatuses analyze analysis samples from a plurality of sites in ICP analysis or in MP analysis, the sites and the analysis apparatuses are at a distance, and a transferring distance may lengthen. In this case, there is a risk that the loss and the contamination occur in an analysis sample, and additionally the flow rate at which the transfer can be made is limited due to pressure loss, during a long-distance transfer in transferring the analysis sample in a liquid state. Reducing the inner diameter of a pipe through the analysis sample is transferred, increases the flow rate of the analysis sample, to some extent. In this case, the pressure loss increases, and a high pressure pump is required. Using the high-pressure pump is unfavorable for trace element analysis, such as the ICP analysis or the MP analysis, because of a cause of the contamination of the analysis sample.

The system in Patent Document 2 can shorten the time necessary for cleaning the spray chamber, but cannot omit a cleaning process itself so that when different analysis samples are transferred from a plurality of sites so as to be analyzed, a switch of the types of the analysis samples cannot be promptly made.

Therefore, the present invention provides an analysis system capable of online transferring an analysis sample at a place apart from an analysis apparatus, and capable of analyzing the analysis samples supplied from at least two sites, with one or a small number of the analysis apparatuses, on a premise that a memory effect is reduced in introducing paths of the analysis samples. The present invention provides the analysis system in which loss or contamination of the analysis samples due to contact with a laying pipe in transferring the analysis samples, barely occurs during the online transfer.

Means for Solving the Problems

In consideration of the above background, the present inventors earnestly examined an analysis system including no component having a dead volume portion, such as a pump or a valve, provided in a transferring path of an analysis sample, the analysis system configured to make the samples barely mix even in analyzing the plurality of the analysis samples.

In consideration of a risk when the analysis samples in a liquid state were transferred, in the examination, a transferring method was based on an analysis system that temporarily atomized the analysis samples in the liquid state collected at sites, and online transferred the analysis samples in a fog state to an ICP analysis apparatus or an MP analysis apparatus. A sample in a fog state can increase a transferring speed in comparison to a sample in a liquid state, and transfer can be made in a short time even over a long distance. Accordingly, it was conceived that the analysis samples in a fog state could be applied even when the analysis samples were transferred over a long distance. Therefore, preventing the analysis samples from mixing, in analyzing the plurality of the analysis samples that had been online transferred, with one or a small number of the analysis apparatuses (the ICP analysis apparatus or the MP analysis apparatus), was earnestly examined.

The present invention based on the examination, relates to an analysis system including: a sample individually transferring unit including a nebulizer that atomizes an analysis sample, a spray chamber that selects the atomized analysis sample based on a particle diameter, and a sample transferring path that online transfers the analysis sample from the spray chamber to a plasma torch; and a common analysis unit including the plasma torch that supplies the online-transferred analysis sample, into plasma flames, and an analysis apparatus with inductively-coupled plasma or microwave plasma. At least a pair of the sample individually transferring units is provided and each of the sample transferring paths of the sample individually transferring units is coupled to the plasma torch of the common analysis unit. Each of the sample transferring paths has a main flow path that transfers the analysis sample from the spray chamber to the plasma torch, a makeup gas supply path that supplies makeup gas to the main flow path, and a drain flow path interposed between the makeup gas supply path and the spray chamber, the drain flow path that discharges the makeup gas and/or the analysis sample from the main flow path. The main flow path includes no pump or valve in a transferring path of the analysis sample. The plasma torch has a sample-introducing pipe that introduces the atomized analysis sample. The inner diameter ($D_d$) of the drain flow path is equivalent to or larger than the inner diameter ($D_t$) of the sample-introducing pipe of the plasma torch near the side of plasma introduction ($D_d=D_t$ or $D_d>D_t$).

In the present invention, even when the configuration including no valve or pump is adopted, a plurality of the analysis samples barely mixes. For a sample transferring path with a common analysis stage being performed and a sample transferring path with the common analysis stage being not performed, adjusting the supply of the makeup gas can also inhibit the samples from mixing.

The analysis system of the present invention includes the sample individually transferring unit installed for each supply source of the analysis samples, and online transfers the plurality of the analysis samples that has been atomized, to the common analysis unit through the individual sample transferring paths. Each of the analysis samples in the fog state can be transferred at a flow rate of approximately 0.5 to 1.5 L/min. Even when, for example, a distance of approximately 100 m is provided between each of the supply sources and the analysis apparatus, each of the analysis samples can be transferred at a speed of approximately 0.5 to 1.5 L/min to be analyzed. In contrast to this, when each of the analysis samples is transferred, remaining in a liquid state, the transferring speed is required to be one several-hundredth in consideration of an increase in pressure inside a laying pipe. Generally, there is a difference approximately several-hundred times in density between the samples in the fog state (in a gas state) and the samples in the liquid state.

Each configuration of the analysis system of the present invention will be described in detail below.

The analysis system of the present invention includes at least two sample individually transferring units, and the sample individually transferring units each have the nebulizer, the spray chamber, and the sample transferring path. The number of the sample individually transferring units that can be installed, is arbitrarily selected in response to the number of the supply sources of the analysis samples. The type of the nebulizer or the type of the spray chamber included in each of the sample individually transferring units may be identical, or may be appropriately and differently selected in accordance with each of the analysis samples to be transferred.

Note that, the analysis system having the one analysis apparatus, will be described in detail in the following descriptions. However, a plurality of the analysis systems of the present invention, is installed in a site in which at least a pair of the analysis apparatuses can be installed, and the number of the sample transferring paths increases so that the number of the analysis samples that can be online transferred can simply increase.

Any of a coaxial type (a concentric type) and an orthogonal type (a cross-flow type) can be applied to the nebulizer that atomizes the analysis sample in a liquid state supplied from the supply source in each of the sample individually transferring units, and the coaxial type is preferable. The material of the nebulizer is not particularly limited, and a quartz-made or PFA-made material is preferably selected in accordance with the properties of the analysis sample in the supply source.

Any of a Scott type spray chamber having a high capacity of selecting fog and a cyclone type spray chamber in which plasma is favorably introduced, with high sensitivity, can be applied to the spray chamber that selects the atomized analysis sample, based on a particle diameter. The material of the spray chamber is not limited, and a Pyrex (registered trademark)-made, quartz-made, polypropylene-made, or PFA-made material can be applied. The material is preferably selected in accordance with the properties of the analysis sample in the supply source.

Each of the sample individually transferring units preferably includes a desolvation device to make the atomized analysis sample, have a further finer particle diameter. In this case, the spray chamber is arranged in the desolvation device. The desolvation device typically includes a mechanism that heats and cools the spray chamber, provided. The spray chamber is heated so that a solvent in the analysis sample evaporates and the particle diameter of the sample that has been atomized decreases. As a result, a sample component being an object to be analyzed can be concentrated. For the analysis sample concentrated with the desolvation device, a distance over which the sample component can be transferred without being sedimented, lengthens. For example, the transfer can be made at a flow rate of approximately 0.5 to 1.5 L/min.

The sample transferring path through which the analysis sample in the fog state selected by the spray chamber is online transferred, has the main flow path, the makeup gas supply path, and the drain flow path. Each of the sample transferring paths for online transferring at least a pair of the analysis samples, is coupled to the one plasma torch, and the plurality of the analysis samples can be analyzed with the one analysis apparatus. As described above, the main flow path including no pump or valve, can prevent a memory from occurring and can prevent the analysis samples from mixing. The length of the main flow path can be arbitrarily selected in response to a distance from the supply source to the analysis apparatus. The inner diameter (the diameter) of a laying pipe of the main flow path can be, for example, approximately 3 to 6 mm.

The drain flow path is provided between the makeup gas supply path and the spray chamber, and is capable of discharging the analysis sample and the makeup gas that flow through the main flow path. The drain flow path preferably has a valve openable and closable. The analysis system of the present invention includes at least two sample individually transferring units and one common analysis unit, is capable of successively analyzing the plurality of the analysis samples, with the one analysis apparatus, and also is capable of successively supplying the different analysis samples to the plasma torch. That is, the analysis due to the analysis system of the present invention requires a mechanism capable of discharging the remaining analysis sample, out of the path, without being introduced to the plasma torch while the analysis sample is supplied from one sample transferring path out of the at least two sample transferring paths to the plasma torch. Therefore, the analysis system of the present invention, includes the drain flow path provided to each of the sample transferring paths to discharge the analysis sample and the makeup gas in response to a supply condition of the plasma torch. The drain flow path in at least one of the sample transferring paths, preferably has a reducing portion that reduces a flow path space. When the reducing portion is provided, a tendency occurs that the analysis samples are easily prevented from mixing, to be described later.

The makeup gas supply path supplies the appropriate makeup gas to each main flow path in the at least two sample individually transferring units. As with typical ICP analysis, the makeup gas is used for adjusting the concentration of the analysis sample, by makeup gas supply, to adjust the analysis sample to be introduced to the plasma torch, for optimum sensitivity. Additionally, the makeup gas has a function of preventing the analysis samples from mixing, to be described in detail below. The inner diameter (the diameter) of a laying pipe for the makeup gas is preferably, approximately 1.5 to 4 mm. A configuration in which argon gas or mixed gas of argon gas and oxygen can be supplied as the makeup gas, is provided.

The plurality of the sample individually transferring units is provided in response to the number of the supply sources of the analysis samples, whereas only the one common analysis unit is provided in the analysis system of the present invention. The common analysis unit includes the one plasma torch and the one analysis apparatus. The respective sample transferring paths are coupled to the plasma torch, and the sample individually transferring units can transfer the analysis samples, to the common analysis unit.

The plasma torch in the common analysis unit has the sample introducing pipe that introduces the atomized analysis sample, and the makeup gas. A triple pipe or a quadruple pipe that is generally known, can be applied to the plasma torch, and any of an integrated torch and a separable torch (a demountable torch) that can separate a torch injector, can be applied. As a typical shape, a gas pipe for forming plasma and a gas pipe for cooling are provided around the sample introducing pipe provided at a substantially center. The sample introducing pipe coupled to the main flow paths, near an outlet from which the plasma is introduced, typically has an inner diameter of approximately 1.0 to 2.5 mm. The inner diameter of the sample introducing pipe near the outlet is small so that the plasma can be efficiently introduced.

The plasma torch is coupled to the analysis apparatus with the inductively-coupled plasma (the ICP analysis apparatus) or the analysis apparatus with the microwave plasma (the MP analysis apparatus), and the analysis of the analysis samples can be made. An inductively-coupled plasma mass spectrometry apparatus or an inductively-coupled plasma optical emission spectrometry apparatus can be applied as the ICP analysis apparatus, and the inductively-coupled plasma mass spectrometry apparatus is preferable. A microwave plasma atomic emission spectrometry (MP-AES) apparatus can be applied as the microwave plasma analysis apparatus. The configuration of the ICP analysis apparatus or MP analysis apparatus is not particularly limited, and an arbitrary ICP analysis apparatus or MP analysis apparatus can be applied.

Here, as described above, the analysis system of the present invention is capable of successively supplying the analysis samples, different from each other, to the one plasma torch so that a sample being analyzed preferably easily flows to the plasma torch and a sample not to be analyzed preferably flows to the side of the drain flow path opposite to the plasma torch for the analysis samples in the sample transferring paths. This is because the analysis samples are prevented from mixing on the periphery of the plasma torch. Here, as described above, the present invention removes the use of the pump to be a cause of memory occurrence in each of the transferring paths of the analysis samples, and an active flow to the side of the plasma torch is difficult to generate. Based on the above point, to adjust the flow of each of the analysis samples to the side of the plasma torch and the flow of each of the analysis samples to the drain flow path, the relationship between the flows was determined in the analysis system of the present invention.

Specifically, in the analysis system of the present invention, the inner diameter ($D_d$) of each of the drain flow paths is equivalent to or larger than the inner diameter ($D_t$) of the sample introducing pipe of the plasma torch near a plasma introducing pipe. In the above configuration, the analysis sample and the makeup gas flowing through the main flow path, tend to easily flow to the drain flow path having low laying pipe resistance rather than in a direction of the sample introducing pipe, having high laying pipe resistance, of the plasma torch. In contrast, the sample not to be supplied to the plasma torch tends to actively and easily flow to the drain flow path, and the analysis samples are easily prevented from mixing.

The analysis system can online transfer the analysis samples and can acquire an analysis result. Some types of the analysis samples may require pretreatment such as dilution or addition of a standard sample. For the addition of the standard sample, the analysis system of the present invention, preferably has a standard sample adding device that adds the standard sample to the analysis sample before the atomization with the nebulizer. The standard sample adding device adds the standard sample having a known concentration in a certain quantity to the analysis sample in a certain quantity so that a standard addition method to be described later can quantitatively determine the analysis sample. Here, the standard sample adding device preferably includes no pump or valve that may generate a memory in a dead volume, provided in a flow path for quantitatively determining the analysis sample, as with the main flow paths.

The analysis system of the present invention can include a sample diluting unit that dilutes the analysis sample before the atomization with the nebulizer. An arbitrary configuration can be applied as the sample diluting unit, and a configuration including no pump or valve that may generate a memory in a dead volume, is preferable.

The analysis system of the present invention described above can be applied to an analysis method below. That is, the analysis system can be applied to an analysis method including the steps of: online transferring an analysis sample through a sample-transferring path from a spray chamber to a plasma torch after a nebulizer atomizes the analysis sample and the spray chamber selects the atomized analysis sample based on a particle diameter; and performing a common analysis with inductively-coupled plasma or microwave plasma to the analysis sample with an analysis apparatus by supplying the online-transferred analysis sample into plasma flames by the plasma torch. The step of online transferring individually online transfers the analysis samples through at least a pair of the sample transferring paths, supplies any one of the analysis samples to the plasma torch, and alternately supplies each of the analysis samples to a common analysis stage. The online transfer transfers the analysis samples through main flow paths from the spray chambers to the plasma torch, supplies makeup gas to the main flow paths through makeup gas supply paths, and discharges the makeup gas and/or the analysis samples through drain flow paths. When the sample-transferring path of the analysis sample during the step of performing the common analysis is performed is defined as an action path, and the sample-transferring path of the analysis sample during the step of performing the common analysis is not performed is defined as a standby path, only the makeup gas is supplied between the makeup gas supply path and a path end portion on the side of the plasma torch, in the standby path.

As described above, the analysis method of the present invention makes a state where only the makeup gas is supplied to the side of the plasma torch for the sample transferring path (the standby path) of the analysis sample with a common analysis unit for the transfer to the plasma torch, being not performed. Therefore, only the analysis sample (the analysis sample in the action path), to be analyzed, easily flows to the plasma torch. Specifically, only the makeup gas is supplied between the makeup gas supply path and a path end portion on the side of the plasma torch (a junction of the standby path and the action path), in the standby path, and the analysis sample of the standby path is not supplied. Appropriately adjusting the supply of the makeup gas in each of the standby path and the action path, can supply the flow of the makeup gas in the standby path, as described above.

Here, the descriptions will be given in that the analysis samples can be prevented from mixing, due to the supply of the makeup gas as described above in the analysis method of the present invention. In the analysis method of the present invention, the analysis sample in the action path and the makeup gas in the action path mix to be supplied to the plasma torch. In this case, the makeup gas in the standby path is partially supplied to the side of the plasma torch and additionally most of the remains flow to the side of a sample supply source to discharge through the drain path. In this manner, the makeup gas flows from the makeup gas supply path to the drain flow path in the standby path. Therefore, the analysis sample in the standby path discharges through the drain flow path not to flow to the side of the makeup gas supply path.

Furthermore, when the analysis system having the inner diameter ($D_d$) of each of the drain flow paths equivalent to or larger than the inner diameter ($D_t$) of the inlet portion of the sample introducing pipe of the plasma torch ($D_d=D_t$ or $D_d>D_t$), is applied to the analysis method of the present invention, the makeup gas flow is further easily controlled to be made. The makeup gas easily flows to the side of the drain flow path having low pressure, and the prevention of the analysis samples from mixing is easily achieved as described above.

In the analysis system of the present invention, a standard sample is preferably added to the analysis sample before the atomization with the nebulizer, and the standard addition method preferably adds the standard sample. The standard addition method prepares a sample for a calibration curve, including the standard sample in a different quantity added to the analysis sample in a certain quantity, having an element concentration unknown, and quantitatively determines the element concentration based on the relationship between the concentration of the standard sample that has been added and the signal intensity of the analysis apparatus. Thus, a variation in the sensitivity of the analysis apparatus is corrected, and an accurate analysis result can be acquired. Note that, in addition to the standard addition method, an internal standard method is also known as a method of correcting the variation in the sensitivity of the analysis apparatus, and is similar to a measurement element. The method adds an internal standard material to which a separate measurement can be made except an object to be measured, to a standard sample and an unknown sample, and generates a calibration curve between the signal intensity ratio and concentration between the internal standard material and the standard sample. The method is unfavorable for the analysis of the analysis sample to be online transferred.

Advantageous Effects of the Invention

The analysis system of the present invention can achieve prompt feedback to sites in response to analysis results acquired from the atomized analysis sample and been online transferred. The one analysis apparatus analyzes the analysis samples supplied from at least a pair of the supply sources to be easily applied as an analysis system including the ICP analysis apparatus or the MP analysis apparatus. A plurality of the analysis samples barely mixes in each transferring path, and an accurate analysis result can be acquired.

DESCRIPTION OF EMBODIMENTS

An embodiment of the present invention will be described below.

Figure 1:
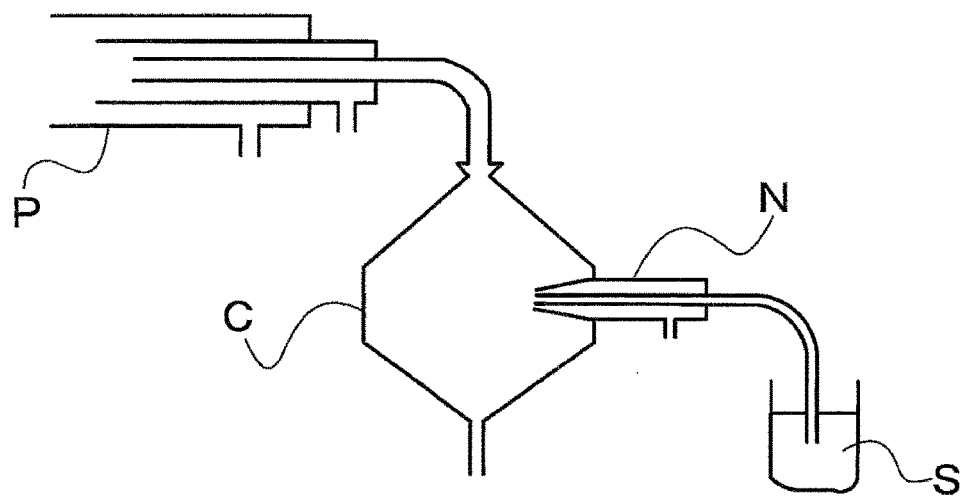
FIG. 1 is a schematic view of conventional exemplary introduction of a sample solution.
Figure 2:
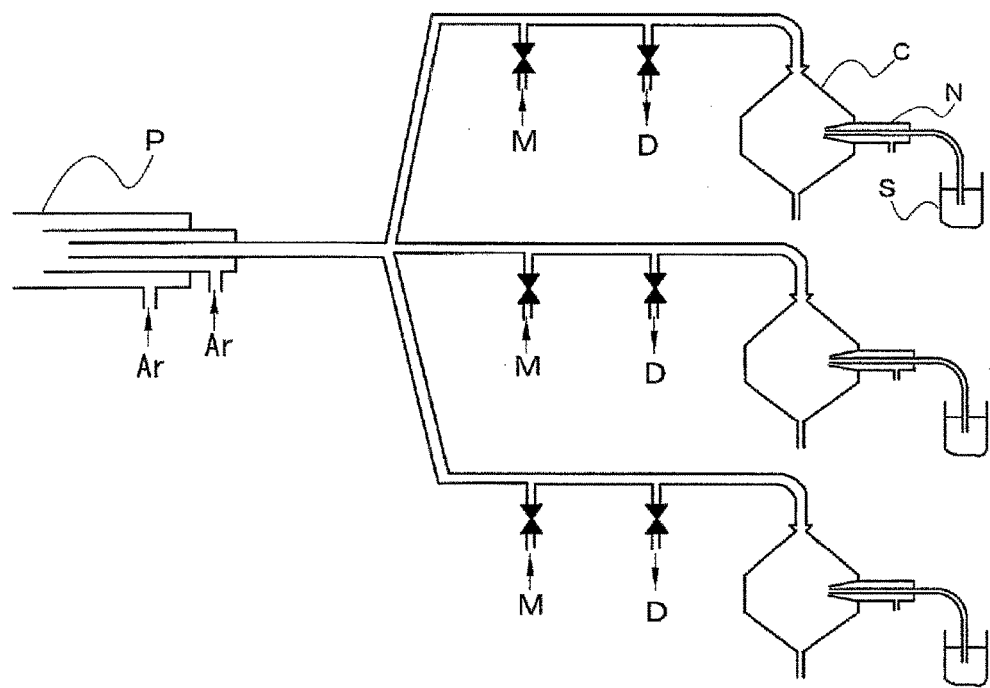
FIG. 2 is a schematic view of an analysis system in an embodiment.

An analysis system illustrated in FIG. 2 online transferred analysis samples sampled from different three places and then an ICP analysis apparatus analyzed the analysis samples. The analysis system can individually supply three types of sample solutions S to be described below, to a common plasma torch P through nebulizers N, spray chambers C, and sample transferring paths, each being independent. Each of the sample transferring paths includes a drain D path and a makeup gas M path. The inner diameter ($D_d$) of each drain flow path satisfies the following expression: $D_d>D_t$ with respect to the inner diameter ($D_t$) of a sample introducing pipe of the plasma torch near the side of plasma introduction. Each of the drain flow paths has a reducing portion.

Figure 3:
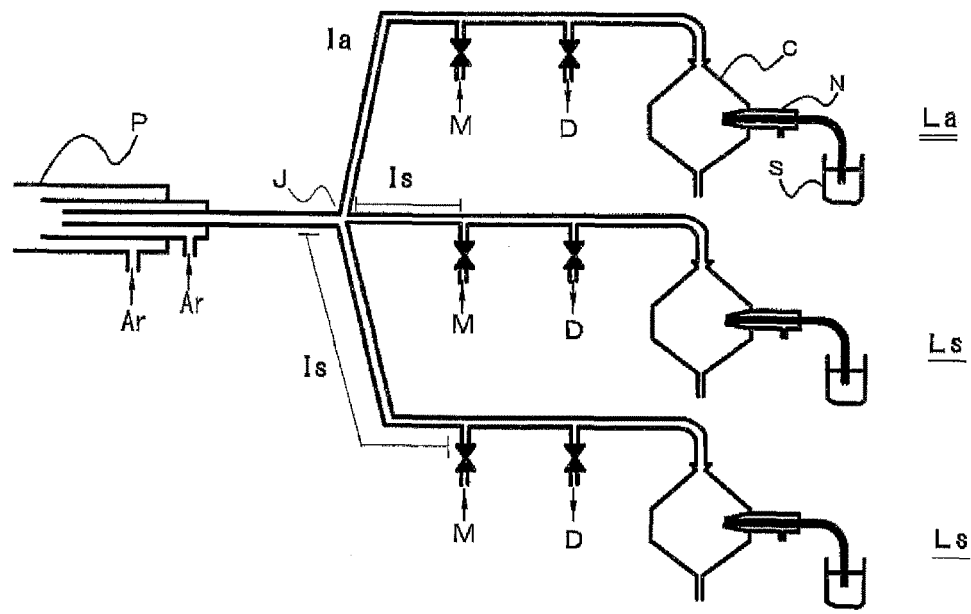
FIG. 3 shows explanatory figures illustrating an analysis method in the embodiment.
Figure 3:
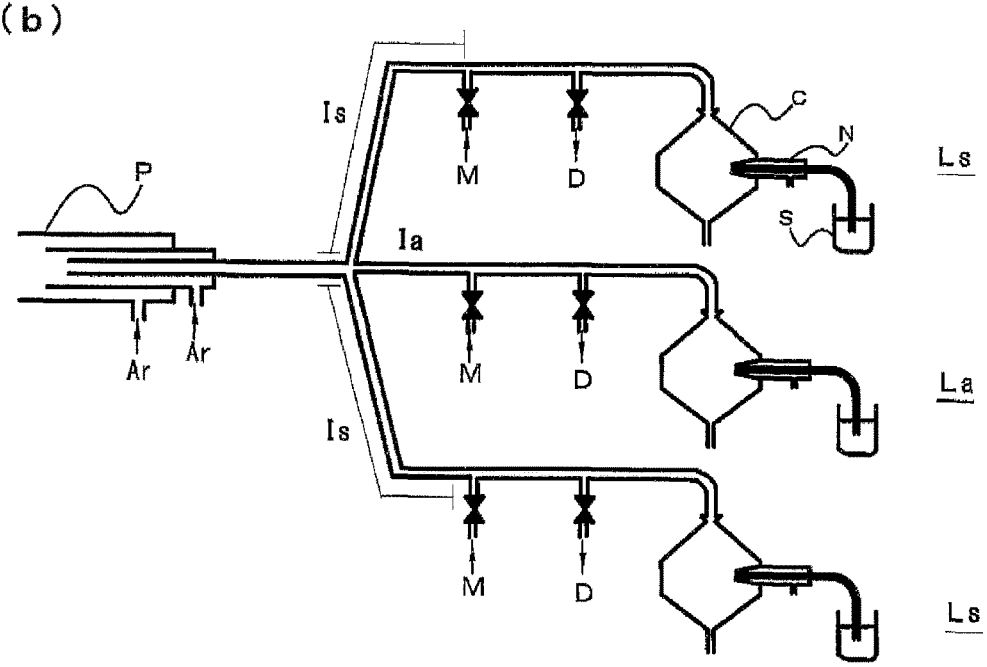

The sample solutions S included sample 1, sample 2, and sample 3 defined as an Rh solution having a concentration of 1 ppb, a Y solution having a concentration of 1 ppb, and an In solution having a concentration of 1 ppb, respectively. The sample solutions S were analyzed. FIGS. 3(a) and 3(b) are schematic views illustrating before and after a switch of an action path La and a standby path Ls is made. A sample transferring path of an analysis sample with a common analysis unit not being performed (the standby path Ls) was analyzed in a condition in which only the makeup gas was supplied to and the analysis sample of the standby path Ls was not supplied to a portion Is between a makeup gas supply path and a path end portion on the side of the plasma torch (a junction J between the standby path and the action path). With the method, time necessary for stabilizing a signal was measured in making a switch of the analysis samples.

As a result, when the analysis system measured three types of the analysis samples, being switched, the signal decreased from 1 ppb to 10 ppt within fifteen seconds after the switching. The signal of a sample after the switching, stabilized at 1 ppb in approximately fifteen seconds after that. In this manner, the analysis system can make a switch of the supply of the analysis samples including a plurality of the types, in a short time, and can perform the analysis with the one analysis apparatus.

INDUSTRIAL APPLICABILITY

The analysis system of the present invention is suitable when a trace element is online analyzed for quality control in various factories or for environmental analysis of a river. Particularly, the analysis system can analyze analysis samples supplied from at least two supply sources with one analysis apparatus, and is suitable for trace element analysis due to ICP analysis or MP analysis.

REFERENCE SINGS LIST

S sample solution
N nebulizer
C spray chamber
P plasma torch
D drain
Ar argon gas
M makeup gas
La action path
Ls standby path
J junction

The invention claimed is:
1. An analysis system comprising:
a sample individually transferring unit comprising a nebulizer that atomizes an analysis sample, a spray chamber that selects the atomized analysis sample based on a particle diameter, and a sample-transferring path that online transfers the analysis sample from the spray chamber to a plasma torch; and a common analysis unit comprising the plasma torch that supplies the online-transferred analysis sample, into plasma flames, and an analysis apparatus with inductively-coupled plasma or microwave plasma, wherein at least a pair of the sample individually transferring units is provided and each of the sample transferring paths of the sample individually transferring units is coupled to the plasma torch of the common analysis unit, each of the sample transferring paths has a main flow path that transfers the analysis sample from the spray chamber to the plasma torch, a makeup gas supply path that supplies makeup gas to the main flow path, and a drain flow path interposed between the makeup gas supply path and the spray chamber, the drain flow path that discharges the makeup gas and/or the analysis sample from the main flow path, the main flow path includes no pump and valve in a transferring path of the analysis sample, the plasma torch has a sample introducing pipe that introduces the atomized analysis sample, and the inner diameter ($D_d$) of the drain flow path is equivalent to or larger than the inner diameter ($D_t$) of the sample introducing pipe of the plasma torch near the side of plasma introduction ($D_d=D_t$ or $D_d>D_t$).

2. The analysis system according to claim 1, wherein the drain flow path in at least one of the sample transferring paths has a reducing portion that reduces a flow path space.

3. The analysis system according to claim 2, wherein the sample individually transferring units each comprise a desolvation device, and the spray chamber is arranged in the desolvation device.

4. The analysis system according to claim 3, further comprising: a standard sample adding device that adds a standard sample to the analysis sample before the atomization due to the nebulizer.

5. The analysis system according to claim 2, further comprising: a standard sample adding device that adds a standard sample to the analysis sample before the atomization due to the nebulizer.

6. The analysis system according to claim 1, wherein the sample individually transferring units each comprise a desolvation device, and the spray chamber is arranged in the desolvation device.

7. The analysis system according to claim 6, further comprising: a standard sample adding device that adds a standard sample to the analysis sample before the atomization due to the nebulizer.

8. The analysis system according to claim 1, further comprising: a standard sample adding device that adds a standard sample to the analysis sample before the atomization due to the nebulizer.

9. An analysis method comprising the steps of:
online transferring an analysis sample through a sample transferring path from a spray chamber to a plasma torch after a nebulizer atomizes the analysis sample and the spray chamber selects the atomized analysis sample based on a particle diameter; and performing a common analysis with inductively-coupled plasma or microwave plasma to the analysis sample with an analysis apparatus by supplying the online-transferred analysis sample into plasma flames by the plasma torch, wherein the step of online transferring individually online transfers the analysis samples through at least a pair of the sample transferring paths, supplies any one of the analysis samples to the plasma torch, and alternately supplies each of the analysis samples to the common analysis step, the online transfer transfers the analysis samples through main flow paths from the spray chambers to the plasma torch, supplies makeup gas to the main flow paths through makeup gas supply paths, and discharges the makeup gas and/or the analysis samples through drain flow paths, and when the sample transferring path of the analysis sample during the step of performing the common analysis is performed is defined as an action path, and the sample transferring path of the analysis sample with the step of performing the analysis, being not performed, is defined as a standby path, only the makeup gas is supplied between the makeup gas supply path and a path end portion on the side of the plasma torch, in the standby path.

10. The analysis method according to claim 9, wherein a standard addition method adds a standard sample to the analysis sample before the atomization.

* * * * *